(12) United States Patent
Collino et al.

(10) Patent No.: US 9,341,615 B2
(45) Date of Patent: *May 17, 2016

(54) PC-O 40:1 AS A BIOMARKER FOR HEALTHY AGING

(71) Applicant: Nestec S.A., Vevey (CH)

(72) Inventors: Sebastiano Collino, Lausanne (CH);
Ivan Montoliu Roura, Lausanne (CH);
Francois-Pierre Martin, Vuisternens-devant-Romont (CH);
Philippe Alexandre Guy, Lucens (CH);
Serge Andre Dominique Rezzi, Semsales (CH)

(73) Assignee: NESTEC S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/491,557

(22) Filed: Sep. 19, 2014

(65) Prior Publication Data
US 2015/0072320 A1 Mar. 12, 2015

Related U.S. Application Data

(63) Continuation of application No. PCT/EP2013/054332, filed on Mar. 5, 2013.

(30) Foreign Application Priority Data

Mar. 22, 2012 (EP) .................................. 12160735

(51) Int. Cl.
| | | |
|---|---|---|
| *G01N 33/49* | (2006.01) | |
| *G01N 33/493* | (2006.01) | |
| *G09B 19/00* | (2006.01) | |
| *G01N 33/92* | (2006.01) | |
| *G01N 33/68* | (2006.01) | |

(52) U.S. Cl.
CPC .............. *G01N 33/49* (2013.01); *G01N 33/492* (2013.01); *G01N 33/493* (2013.01); *G01N 33/6893* (2013.01); *G01N 33/92* (2013.01); *G09B 19/00* (2013.01); *G09B 19/0092* (2013.01); *G01N 33/6848* (2013.01); *G01N 2405/06* (2013.01); *G01N 2570/00* (2013.01); *G01N 2800/04* (2013.01); *G01N 2800/50* (2013.01); *G01N 2800/7042* (2013.01); *G01N 2800/7095* (2013.01)

(58) Field of Classification Search
CPC .............. G01N 33/68; G01N 33/6893; G01N 33/6842; G01N 33/6848; G01N 33/48; G01N 33/49; G01N 33/492; G01N 33/493; G01N 33/92; G01N 2570/00; G01N 2800/00; G01N 2800/04; G01N 2800/32; G01N 2800/50; G01N 2800/60; G01N 2800/7042; G01N 2800/7095; G01N 2405/06; Y10T 436/17; Y10T 436/173845; Y10T 436/18; Y10T 436/182; Y10T 436/200833; Y10T 436/203332; Y10T 436/24; G09B 19/00; G09B 19/0092
USPC ......... 436/63, 71, 86, 89, 106, 111, 128, 131, 436/173, 119, 120; 434/127, 236; 562/448; 554/80; 73/61.43
See application file for complete search history.

(56) References Cited

U.S. PATENT DOCUMENTS

| | | |
|---|---|---|
| 2008/0124752 A1 | 5/2008 | Ryals et al. |
| 2009/0155826 A1 | 6/2009 | Hu et al. |
| 2012/0129265 A1* | 5/2012 | Lundin et al. .................... 436/89 |
| 2012/0202240 A1* | 8/2012 | Deigner et al. ................. 435/29 |
| 2014/0343865 A1 | 11/2014 | Brown et al. |
| 2015/0010673 A1 | 1/2015 | Collino et al. |
| 2015/0065366 A1 | 3/2015 | McDunn et al. |
| 2015/0072043 A1 | 3/2015 | Collino et al. |
| 2015/0072363 A1 | 3/2015 | Collino et al. |
| 2015/0105296 A1 | 4/2015 | Collino et al. |

FOREIGN PATENT DOCUMENTS

| | | |
|---|---|---|
| EP | 2249161 | * 11/2010 |
| WO | 2011/010104 A1 | 1/2011 |
| WO | 2011/063470 A1 | 6/2011 |
| WO | 2011/140093 A2 | 11/2011 |

OTHER PUBLICATIONS

Romisch-Margl et al. Metabolomics, vol. 8(1), Mar. 12, 2011, pp. 133-142.*
Caprari, P. et al., "Aging and red blood cell membrane: a study of centenarians," Experimental Gerontology, 34(1):47-57, 1999.
Collino, S. et al., "Monitoring healthy metabolic trajectories with nutritional metabonomics," Nutrients, 1(1): 101-110, 2009.
Gieger, C. et al., "Genetics meets metabolomics: a genome-wide association study of metabolite profiles in human serum," PLOS Genetics, 4(11):e1000282, 12 pages, 2008.

(Continued)

*Primary Examiner* — Maureen Wallenhorst
(74) *Attorney, Agent, or Firm* — Kilpatrick Townsend & Stockton LLP

(57) ABSTRACT

Using NMR/MS based metabonomics and targeted lipidomics approaches the inventors have explored the metabolic phenotypes of aging and longevity in a cohort including centenarians, elderly and young adults. The inventors have identified biomarkers for a reduced risk of developing ageing related chronic inflammatory disorders and propose a method of diagnosing a lifestyle that allows delaying and/or avoiding ageing related chronic inflammatory disorders using PC-O 40:1 as biomarker.

18 Claims, 8 Drawing Sheets

(56) References Cited

OTHER PUBLICATIONS

Helmholtz Zentrum München, "Parameters at the Metabolic Platform of the Genome Analysis Center," Jan. 1, 2009, German Research Centre for Environmental Health (GmbH), Metabolomic Platform, Genome Analysis Center, Institute of Experimental Genetics, Neuherberg, Germany, retrieved online from <http://www.helmholtz-muenchen.de/fileadmin/GAC/Metabolomics/Parameters_Metabolomics_GAC.pdf> on Jun. 26, 2012, 6 pages.

Linnane, A. et al., "Healthy aging: regulation of the metabolome by cellular redox modulation and prooxidant signaling systems: the essential roles of superoxide anion and hydrogen peroxide," Biogerontology, 8(5):445-467, 2007.

Rhee, E. et al., "Lipid profiling identifies a triacylglycerol signature of insulin resistance and improves diabetes prediction in humans," Journal of Clinical Investigation, 121(4):1402-11, 2011.

Biagi, E. et al., "Ageing of the human metaorganism: the microbial counterpart," Age: Journal of the American Aging Association, 34(1):247-267, 2011.

Feldstein, A. et al., "Mass spectrometric profiling of oxidized lipid products in human nonalcoholic fatty liver disease and nonalcoholic steatohepatitis," Journal of Lipid Research, 51(10):3046-54, 2010.

Giunta, S., "Is inflammaging an auto[innate]immunity subclinical syndrome?" Immunity & Ageing, 3:12, 2006. (2 pages).

Shearer, G. et al., "Lipoprotein lipase releases esterified oxylipins from very low-density lipoproteins," Prostaglandins Leukotrienes and Essential Fatty Acids, 79(6):215-222, 2008.

Yang, J. et al., "Quantitative profiling method for oxylipin metabolome by liquid chromatography electrospray ionization tandem mass spectrometry," Analytical Chemistry, 81(19):8085-93, 2009.

Yap, I. et al., "Metabolome-wide association study identifies multiple biomarkers that discriminate North and South Chinese populations at differing risks of cardiovascular disease: INTERMAP Study," Journal of Proteome Research, 9(12):6647-54, 2010.

* cited by examiner

PC-O 40:1 AS A BIOMARKER FOR HEALTHY AGING

The present application is a continuation of PCT/EP2013/054332, filed Mar. 5, 2013, which application claims priority to European Application No. 12160735.2, filed Mar. 22, 2012, and the disclosure of each such application is hereby incorporated by reference in its entirety for all purposes.

The present invention generally concerns a healthy lifestyle and the prevention of ageing related chronic disorders. In particular, the present invention concerns biomarkers and their use to detect improvements in lifestyle. As such, the present invention provides for example 1-O-alkyl-2-acylglycerophosphocholine (PC-O) 40:1 as a biomarker and a method for diagnosing a lifestyle that allows delaying and/or avoiding ageing related chronic inflammatory disorders that uses the biomarker 1-O-alkyl-2-acylglycerophosphocholine (PC-O) 40:1.

Aging is defined as the time-dependent decline of functional capacity and stress resistance, associated with increased risk of morbidity and mortality. Additionally, the aging phenotype in humans is very heterogeneous and can be described as a complex mosaic resulting from the interaction of a variety of environmental, stochastic and genetic-epigenetic variables. Decades of research on aging have found hundreds of genes and many biological processes that are associated to the aging process, but at the same time, many fundamental questions are still unanswered or are object of intense debate.

These questions are frequently not addressable by examining a single gene or a single pathway, but are better addressed at a systemic level, capturing aging as a complex multi-factorial process. Moreover, ageing is accompanied by a chronic, low grade, inflammatory status, resulting from an imbalance between pro- and anti-inflammatory processes, a pathogenic condition that has been revealed critical in the onset of major age-related chronic diseases such as atherosclerosis, type 2 diabetes, and neuro-degeneration.

Within this perspective, acquired healthy aging and longevity are likely the reflection of not only a lower propensity to accumulate inflammatory responses, but also of efficient anti-inflammatory network development. In addition, there is a growing awareness of the importance of the variation in the gut microbiota as its effects on the host mammalian system, having displayed direct influence in the etiology of several diseases such as insulin resistance, Crohn's disease, irritable bowel syndrome, obesity, and cardiovascular disease.

Metabonomics is considered today a well-established system approach to characterize the metabolic phenotype, which results from a coordinated physiological response to various intrinsic and extrinsic parameters including environment, drugs, dietary patterns, lifestyle, genetics, and microbiome. Unlike gene expression and proteomic data which indicate the potential for physiological changes, metabolites and their kinetic changes in concentration within cells, tissues and organs, represent the real end-points of physiological regulatory processes.

Metabolomics had successfully been applied to study the modulation of the ageing processes following nutritional interventions, including caloric restriction-induced metabolic changes in mice, dogs, and non-human primates. Specifically, in the canine population profound changes in gut microbiota metabolism were associated with ageing. Despite these findings, a comprehensive profiling of the molecular mechanisms affecting the aging process has not yet been reported. Moreover, metabolic phenotyping of longevity is still missing.

Consequently, it was the objective of the present invention to provide the art with a biomarker that can be detected easily and that allows it to diagnose a lifestyle that is likely to permit healthy ageing and that in particular allows to delay and/or avoid ageing related chronic inflammatory disorders.

The present inventors were surprised to see that they could achieve the objective of the present invention by the subject matter of the independent claims. The dependant claims further develop the idea of the present invention.

Using a combined holistic 1H nuclear magnetic resonance (NMR) spectroscopy approach in urine, and targeted mass spectrometry (MS) and lipidomic approaches in serum, the inventors could detect changes in the metabolic profiles of a well defined aging cohort compromising centenarians, elderly, and young adults.

The selected aging group represents a homogeneous population of a restricted geographic area of Northern Italy, compromising young adults (31 years old in average), elderly (70 years old), and centenarians people (100 years old). Among the three aging groups, centenarians are a well accepted model of healthy aging and longevity [Sansoni P, et al., Exp Gerontol. 2008; 43:61-65; Franceschi C, et al., Mech Ageing Dev. 2007; 128:92-105; Cevenini E, et al., Expert Opin Biol Ther. 2008; 8:1393-1405] and their acquired successful aging seems to be driven by an optimal balance between pro-inflammatory and anti-inflammatory forces [Franceschi C, et al., Mech Ageing Dev. 2007; 128:92-105].

The inventors were surprised to find profound differences between the elderly and centenarian phenotypes where dynamics of the interaction between intestinal microbiota and the host, and a neutral balanced of inflammatory responses are much more pronounced in the longevity phenotype.

The inventors have characterized, by using a complementary NMR-MS-based metabolomics and lipidomic approach, in both urine and serum, the metabolic phenotype (metabotype) of aging and longevity.

Centenarians reach the very extremes of the human lifespan because of a unique capability to postpone disease and disability into their later years of life. Classical clinical parameters (Table 1) display that centenarians have very low incidence of insulin-resistance, have anthropometric (BMI), metabolic (cholesterol, LDL-C, HDL-C, triglycerides), values that are optimal for their age. In addition, their cognitive function was measured using the Mini-Mental State Examination (MMSE), displaying low incidence of severe cognitive decline.

Specifically centenarians display a unique metabolic phenotype. Metabolic profiling of urine revealed that the longevity phenotype is highly influenced by the gut microbiome as displayed by a higher excretion of phenylacetylglutamine (PAG), p-cresol sulphate (PCS). The inventors postulate that gut microbiota extensively catabolize protein and aromatic amino acids, including phenylalanine and tyrosine, to form phenylacetylglutamine and p-cresol sulfate.

Comprehensive MS-based targeted metabonomics analysis revealed important biological changes associated to longevity and healthy aging in serum. Furthermore, between the three age groups centenarians are an attractive longevity model to characterize as they reach the very extremes of the human lifespan because of a unique capability to postpone disease and disability into their later years of life. Within age progression the inventors saw a decrease in lysophospatidylcholines (LPC 18:2, LPC 20:4), with their concentration being more reduced in centenarians. Specifically, the decrease in LPC 18:018.0 appears to be specific to centenarians. While it is imperative to note that LPC has different species based on fatty acid chain length and degree of saturation, with different physical and biological properties, phospholipids are generally pro-inflammatory [Aiyar N, et al., Mol Cell Biochem. 2007; 295:113-120], with atherogenic properties [Schmitz G, et al., Atherosclerosis. 2010; 208:10-18], and their increase levels is often seen in patients with type 2 diabetes [Rabini R A, et al., Diabetes. 1994; 43:915-919].

In respect to elderly centenarians display a balanced change in concentration of several acyl-ether PC species with contents of three PC-O species, PC-O 34:3, PC-O 36:4, PC-O 40:1 significantly decreased and two other PC species, PC-O 32:1, PC-O 34:1, being significantly higher. While the physiological role of ether phospholipids is less understood, plasmalogens containing a vinyl ether bond linking the sn-1 aliphatic chain to the glycerol backbone are the most abundant ether phospholipids. Here, the differences in the levels of acyl-ether phosphatidylcholine species might be due to differences in handling oxidative damage.

Within age progression, an increase in sphingomyeline (SM) species is seen with marked increase in SM 24:1 and SM16:0 in centenarians. Yet, the inventors found a specific decrease concentration of SM24:0 and SM-OH 22:1 in centenarians. SM species are important cellular membrane constituents which are tightly associated with cholesterol in construction, metabolism and transport, and which are enriched in lipid rafts. The physiological role of SM is still not clear as previous studies have shown the relationship between elevated SM levels and atherosclerosis [Kummerow F A, et al., J Nutr Biochem. 2001; 12:602-607], while others displayed that plasma sphingomyelin levels were not associated with increased risk of CVD events. Lastly, while there are no significant changes for the levels of most diacyl-phosphatidylcholine species (PC-O), centenarians display alterations in the individual levels of PC-O 36:2.

Changes in contents of PC and PC-O might have an impact on the activity of arachidonic acid metabolites synthesis (prostaglandins, thromboxanes, leukotrienes) which are key mediators and regulators of host physiological reactions, involved in oxidative stress, apoptosis, and modulation of immune and inflammatory functions. Indeed, centenarians display also a unique balanced network of lipid mediators with both anti- and pro-inflammatory properties.

Compared to elderly, a higher concentration of leukotrines, LTB-4 and LTE-4, was seen. Centenarians display higher level of 15-hydroxy-eicosatetraenoic acid (15-HETE), a major product of 15-lipoxygenase (15-LOX) enzyme. 15-HETE inhibits 5-lipoxygenase formation, decreases the production of leukotriene B4 and 12-HETE and suppresses immune reactions. Compared to elderly, increase activation of CYP pathway is also seen in centenarians, with increase generation of 8,9-EpETrE and decrease concentration of 11,12-DiHETrE. EpETrE are important components of many intracellular signaling in both cardiac and extracardiac tissues. Studies have shown that EpETrEs display anti-inflammatory effects by inhibiting the activation of nuclear factor (NF)-κB-mediated gene transcription. In addition, they display thrombolytic and angiogenic properties within the vasculature. EpETrEs can be further metabolized by soluble epoxide hydrolase (sEH) to dihydroxy-eicosatrienoic acids (DiHETrE).

In general, when EpETrEs are metabolized to DiHETrEs by sEH, their biological activities become less pronounced, theeofre here the decrease concentration of 11,12-DHET might revel decrease effect sEH of its precursor 11,12-EpETrE. Centenarians display a marked decrease in 9-HODE, biological active molecule, and a marker of lipid peroxidation, and 9-oxo-HODE, a stable oxidation product of linoleic acid, the generation of which is increased where oxidative stress is increased.

Centenarians displayed a marked decrease in 9-oxo-HODE, a stable oxidation product of linoleic acid, the generation of which is increased where oxidative stress is increased. Most of the linoleic acid exists in esterified forms as PC and cholesteryl linoleate, both are major components of LDL, and are continuously exposed to many kinds of oxidative stresses to generate hydroxy and hydroperoxy species.

Increased levels of lipid oxidation products, such as 9-oxo ODE were previously detected in plasma samples of patients suffering rheumatoid arthritis, and arthrosclerosis.

Further, compared to elderly, centenarians display depletion in eicosapentanoic acid (EPA). While EPA can be synthesized in humans from alpha-linoleic acid or in greater amount directly from oily fish or fish oil supplements, EPA can be transformed into n-3 eicosanoids, which have diverse functions. A depletion of EPA could display an increase biosynthesis of n-3 eicosanoids.

Consequently the present invention relates in part to a method of diagnosing a lifestyle that allows delaying and/or avoiding ageing related chronic inflammatory disorders, comprising
   obtaining a serum sample from a subject
      determining the level of 1-O-alkyl-2-acylglycerophosphocholine (PC-O) 40:1, in the sample, and
      comparing the subject's PC-O 40:1 level to a predetermined reference value,
wherein the predetermined reference value is based on an average serum PC-O 40:1 level in a control population, and wherein a decreased serum PC-O 40:1 level in the sample compared to the predetermined reference value indicates an increased likelihood to delay and/or avoid ageing related chronic inflammatory disorders.

This method has for example the advantage that obtaining serum from a subject is a well established procedure. The actual diagnosis method can be carried out in a serum sample outside the body.

The level of PC-O 40:1 in the sample can be detected and quantified by any means known in the art. For example, mass spectroscopy, e.g, UPLC-ESI-MS/MS, or NMR spectroscopy, e.g. 1H-NMR spectroscopy, may be used. Other methods, such as other spectroscopic methods, chromatographic methods, labeling techniques, or quantitative chemical methods may be used as well.

The predetermined reference value is based on an average serum PC-O 40:1 level in a control population. The control population can be a group of at least 3, preferably at least 10, more preferred at least 50 people with a similar genetic background, age and an average health status.

The control population can also be the same person, so that the predetermined reference value is obtained previously from the same subject. This will allow a direct comparison of the present lifestyle to a previous lifestyle, for example, and improvements can be directly assessed.

Typical ageing related chronic inflammatory disorders are well known to those of skill in the art. A large part of the ageing phenotype is explained by an imbalance between inflammatory and anti-inflammatory networks, which results in the low grade chronic pro-inflammatory status of ageing, "inflamm-ageing" (Candore G., et al., Biogerontology. 2010 October; 11(5):565-73).

Hence the method of the present invention may be used to diagnose the level of inflamm-ageing.

Typical age related inflammatory disorders are atherosclerosis, arthritis, dementia, type 2 diabetes, osteoporosis, and cardiovascular diseases, for example. For example for these disorders inflammation is seen as a possible underlying basis for the molecular alterations that link aging and age related pathological processes (Chung et al., ANTIOXIDANTS & REDOX SIGNALING, Volume 8, Numbers 3 & 4, 2006, 572-581).

PC-O 40:1 may be used as the only marker for the purpose of the present invention.

While PC-O 40:1 as sole marker is effective as a tool for the diagnosis method of the present invention, the quality and/or the predictive power of said diagnosis will be improved, if the diagnosis relies on more than just one marker.

Hence one or more other markers for the likelihood to delay and/or avoid ageing related chronic inflammatory disorders may be used in combination with PC-O 40:1.

The inventors were surprised to see that also other biomarkers can be used to detect the likelihood to delay and/or avoid ageing related chronic inflammatory disorders.

As such the inventors have identified that increased serum concentrations of
1-O-alkyl-2-acylglycerophosphocholine (PC-O) 32:1,
1-O-alkyl-2-acylglycerophosphocholine (PC-O) 34:1,
15-hydroxy-eicosatetraenoic acid (15-HpETE),
Leukotriene E4 (LTE4),
Leukotriene B4 (4LTB), and/or
8,9-epoxyeicosatrienoic (8,9 EpETre)
allow diagnosing a lifestyle that allows delaying and/or avoiding ageing related chronic inflammatory disorders while decreased serum concentrations of
Hydroxy-Sphingomyelin (SM-OH) 22:1,
Lysophosphatidylcholine (LPC) 18:0
Sphingomyeline (SM) 24:0,
1-O-alkyl-2-acylglycerophosphocholine (PC-O) 34:3,
1-O-alkyl-2-acylglycerophosphocholine (PC-O) 36:4,
Phosphatidylcholine (PC) 36:2,
hydroxyoctadecadienoic acid (9-HODE),
9-oxo-octadecadienoic acid (9-oxo-HODE), and/or
11,12-epoxyeicosatrienoic acid (11,12-DiHETre)
allow diagnosing a lifestyle that allows delaying and/or avoiding ageing related chronic inflammatory disorders The individual lipid species were annotated as follows:
[lipid class] [total number of carbon atoms]:[total number of double bonds]. For example, PC 34:1 reflects a phosphatidylcholine species comprising 34 carbon atoms and 1 double bond.

Consequently, in the method of the present invention the precision of the diagnosis may be increased by also assessing whether the concentration of one or more of the following biomarkers PC-O 32:1, PC-O 34:1, 15-HpETE, LTE4, LTB4, 8,9 EpETre is increased in serum, and/or whether the concentration of one or more of the following biomarkers SM-OH 22:1, LPC 18:0, SM 24:0, PC-O 34:3, PC-O 36:4, PC 36:2, 9-HODE, 9-oxo-HODE, 11,12-DiHETre is decreased in serum, compared to a reference value previously obtained.

The method of the present invention may comprise the assessment of at least 2, at least 3, at least 4, at least 5, at least 6, at least 7, or at least 8 biomarkers.

For example, PC-O 40:1 may be assessed along with SM-OH 22:1.

PC-O 40:1 may also be assessed along with SM 24:0.
PC-O 40:1 may be assessed along with LPC 18:0.
PC-O 40:1 may be assessed along with LTE4.
PC-O 40:1 may be assessed along with PC-O 34:1.
PC-O 40:1 may be assessed along with SM-OH 22:1 and SM 24:0.
PC-O 40:1 may be assessed along with SM-OH 22:1, SM 24:0 and PC-O 40:1.

PC-O 40:1 may be assessed along with SM-OH 22:1, SM 24:0, PC-O 40:1, and 9-HODE.
PC-O 40:1 may be assessed along with SM-OH 22:1, SM 24:0, PC-O 40:1, 9-HODE, and 9-oxo-HODE.
PC-O 40:1 may be assessed along with SM-OH 22:1, SM 24:0, PC-O 40:1, 9-HODE, 9-oxo-HODE, and LPC 18:0.
PC-O 40:1 may be assessed along with SM-OH 22:1, SM 24:0, PC-O 34:1, 9-HODE, 9-oxo-HODE, LPC 18:0, and LTE4.

The advantage of assessing more than one biomarker is that the more biomarkers are evaluated the more reliable the diagnosis will become. If, e.g., more than 1, 2, 3, 4, 5, 6, or 7 biomarkers exhibit the elevations or decreases in concentration as described above, this is a strong indication for an increased likelihood to delay and/or avoid ageing related chronic inflammatory disorders.

Consequently, the method of the present invention may further comprise determining the level of at least one of SM-OH 22:1, LPC 18:0, SM 24:0, PC-O 34:1, 9-HODE, 9-oxo-HODE, or LTE4 in the sample, and comparing the subject's level of at least one of SM-OH 22:1, LPC 18:0, SM 24:0, PC-O 34:1, 9-HODE, 9-oxo-HODE, or LTE4 to a predetermined reference value, wherein the predetermined reference value is based on average serum SM-OH 22:1, LPC 18:0, SM 24:0, PC-O 34:1, 9-HODE, 9-oxo-HODE, or LTE4 level in a control population, and wherein a lower serum PC-O 40:1 level in the sample and/or a lower serum SM-OH 22:1, LPC 18:0, SM 24:0, PC-O 34:1, 9-HODE, or 9-oxo-HODE level in the sample compared to the predetermined reference values indicate an increased likelihood to delay and/or avoid ageing related chronic inflammatory disorders, and/or wherein an elevated serum LTE4, PC-O 34:1 level in the sample compared to the predetermined reference values indicates an increased likelihood to delay and/or avoid ageing related chronic inflammatory disorders.

The precision of the diagnosis of the present invention may further be increased by also assessing whether one or more of the following biomarkers PC-O 32:1, 15-HpETE, LTB4, 8,9 EpETre is increased in serum, and/or whether one or more of the following biomarkers PC-O 34:3, PC-O 36:4, PC 36:2, 11,12-DiHETre are decreased in serum, compared to a reference value previously obtained.

The method of the present invention may additionally or alternatively be used to diagnose a lifestyle that permits healthy and/or healthier ageing.

Healthier ageing may be diagnosed by comparing the actual PAG and/or PCS levels of to predetermined reference values, which were obtained previously from the same subject. Hence, in this case the same subject will act as control population and improvements in lifestyle can be seen directly, while eliminating uncertainties originating from slightly different conditions for other average control populations.

The method of the present invention may also be used to diagnose longevity; and/or the likelihood for longevity. This has the advantage that the consequences of a healthier lifestyle can be directly detected, the maintenance of a healthy lifestyle can be monitored and an unhealthy lifestyle can be corrected before the first clinical manifestations of an unhealthy lifestyle occur.

The method of the present invention may further be used alternatively and/or additionally to diagnose to diagnose healthier gut microflora-host interactions. The gut microbiome performs numerous important biochemical functions for the host, and disorders of the microbiome are associated with many and diverse human disease processes (Kinross et al., Genome Medicine 2011, 3:14). Unfavorable gut microflora-host interaction may have many clinical manifestations, such as systemic disease states, e.g., obesity and cardiovascular disease; or intestinal conditions, e.g. inflammatory bowel disease.

The gut microflora-host interactions may be diagnosed in any subject, but it may be of particular importance to monitor healthy microflora-host interactions in adults or in elderly Hence, the healthier gut microflora-host interactions may be to be diagnosed in the elderly.

A subject is considered as "elderly" if it has surpassed the first half of its average expected lifespan in its country of origin, preferably, if it has surpassed the first two thirds of the average expected lifespan in its country of origin, more preferably if it has surpassed the first three quarters of the average expected lifespan in its country of origin, most preferred if it has surpassed the first four fifths of the average expected lifespan in its country of origin.

For example, if the subject is a human, the method of the present invention may be to be carried out in adults of at least 45 years of age, at least 60 years of age, or at least 75 years of age.

The subject to be tested with the method of the present invention may be a human or an animal, in particular a mammal, for example. Typical animals may be companion animals, such as cats or dogs of farm animals, for example.

The method of the present invention may additionally or alternatively be used to detect the consequences of a change in lifestyle. Here it may be advantageous if the PC-O 34:level and optionally the levels of the other biomarkers mentioned herein are compared to the PC-O 34:level and optionally the levels of the other biomarkers obtained previously from the subject, e.g., before the change in lifestyle or earlier during the change in lifestyle.

Hence, the method of the present invention may be to diagnose a healthier lifestyle, wherein the predetermined reference values are based on the serum PC-O 40:1 level and optionally the levels of the other biomarkers obtained from the subject before a change in lifestyle.

The change in lifestyle may be any change, such as a different job, more sleep, less alcohol, more challenges, less stress, less smoking, more sports, a different working and/or living environment, for example.

The change of lifestyle may also be a change in the diet.

The change in the diet may be for example the use of at least one nutritional product that was previously was not consumed or consumed in different amounts.

As such the method of the present invention may be used to test the effectiveness of a new nutritional regimen, of nutritional products and/or of medicaments.

Nutritional products may be for example products that claim to have an effect on healthy ageing and/or on avoiding ageing related chronic inflammatory disorders.

Typically, nutritional products may be food products, drinks, pet food products, food supplements, nutraceuticals, food additives or nutritional formulas.

The level of the biomarkers, such as the PC-O 40:1 level and optionally the levels of the other biomarkers in the sample can be detected and quantified by any means known in the art. For example, mass spectroscopy, e.g, UPLC-ESI-MS/MS, or NMR spectroscopy, e.g. 1H-NMR spectroscopy, may be used.

Other methods, such as other spectroscopic methods, chromatographic methods, labeling techniques, or quantitative chemical methods may be used as well.

The method of the present invention comprises comparing levels of PC-O 40:1 and optionally the other biomarkers of a test subject to predetermined reference values that may be derived from the PC-O 40:1 level in serum and optionally the levels of other biomarkers from comparable control subjects.

The extent of the difference between the subject's PC-O 40:1 level and optionally levels of the other biomarkers and the corresponding control values is also useful for characterizing the extent of the risk and thereby, determining which subjects would benefit most from certain therapies.

The reference value for PC-O 40:1 and optionally for the other biomarkers is preferably measured using the same units used to characterize the level of PC-O 40:1 and optionally the other biomarkers obtained from the test subject. Thus, if the level of the PC-O 40:1 and optionally the other biomarkers is an absolute value such as the units of PC-O 40:1 in µmol/l (µM) the reference value is also based upon the units of PC-O 34:1 in µmol/l (µM) in individuals in the general population or a selected control population of subjects.

Moreover, the reference value can be a single cut-off value, such as a median or mean. Reference values of PC-O 40:1 and optionally the other biomarkers in obtained serum samples, such as mean levels, median levels, or "cut-off" levels, may be established by assaying a large sample of individuals in the general population or the selected population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is incorporated herein by reference.

Skilled artesians will know how to assign correct reference values as they will vary with gender, race, genetic heritage, health status or age, for example.

For example, the predetermined reference mean values may be

2 µM for 1-O-alkyl-2-acylglycerophosphocholine (PC-O) 32:1, 7.80 µM for 1-O-alkyl-2-acylglycerophosphocholine (PC-O) 34:1, 1.25 µg/100 µl serum for 15-hydroxy-eicosatetraenoic acid (15-HpETE), 0.013 µg/100 µl serum for Leukotriene E4 (LTE4), 0.020 µg/100 µl serum for Leukotriene B4 (4LTB), and/or 0.070 µg/100 µl serum for 8,9-epoxyeicosatrienoic (8,9 EpETre)

16.07 µM for Hydroxy-Sphingomyelin (SM-OH) 22:1, 52.00 µM for Lysophosphatidylcholines (LPC) 18:0, 25.00 µM for Sphingomyeline (SM) 24:0, 5.07 µM for 1-O-alkyl-2-acylglycerophosphocholine (PC-O) 34:3, 14.30 µM for 1-O-alkyl-2-acylglycerophosphocholine (PC-O) 36:4, 1.41 µM for 1-O-alkyl-2-acylglycerophosphocholine (PC-O) 40:1, 10.00 µM for Phosphatidylcholine (PC) 36:2, 0.34 µg/100 µl serum for hydroxyoctadecadienoic acid (9-HODE), 0.043 µg/100 µl serum for 9-oxo-octadecadienoic acid (9-oxo-HODE), and/or 0.017 µg/100 µl serum for 11,12-epoxyeicosatrienoic acid (11,12-DiHETre).

Higher or lower values are indicative for an increased likelihood to delay and/or avoid ageing related chronic inflammatory disorders, as detailed above.

The present inventors were also surprised to find further biomarkers in urine for diagnosing a lifestyle that allows delaying and/or avoiding ageing related chronic inflammatory disorders.

As such the inventors have identified that increased urine concentrations of phenylacetylglutamine (PAG) and/or p-cresol sulphate (PCS) allow diagnosing a lifestyle that allows delaying and/or avoiding ageing related chronic inflammatory disorders.

Phenylacetylglutamine (PAG) and/or p-cresol sulphate (PCS) may be assessed following the method of the present invention, with the only difference that a urine sample is used.

A urine sample has the advantage that it can be obtained and analyzed non-invasively.

The predetermined reference values for PAG and PCS can be determined by those of ski line the art and max vary depending on the circumstances. For example, typical reference values may be 63 μmol/mmol creatinine for PCS and 81 μmol/mmol creatinine for PAG in urine. Higher values are indicative for an increased likelihood to delay and/or avoid ageing related chronic inflammatory disorders.

The present invention also extends to the discovery of a new biomarker that can be used in the diagnosis of a lifestyle that allows delaying and/or avoiding ageing chronic inflammatory disorders.

Consequently, the present invention comprises a biomarker for the diagnosis of a lifestyle that allows delaying and/or avoiding ageing chronic inflammatory disorders, wherein the biomarker is PC-O 40:1.

This biomarker may be detected in serum, which has the advantage that samples to be tested can be obtained easily, possible while analyzing serum for other purposes.

Those skilled in the art will understand that they can freely combine all features of the present invention described herein, without departing from the scope of the invention as disclosed. In particular, features described for the method of the present invention may be applied to the biomarker of the present invention and vice versa.

Those skilled in the art will also understand that while the biomarkers and their application in a diagnosis method is described herein as
  diagnosing a lifestyle that allows to delay and/or avoid ageing related chronic inflammatory disorders,
  diagnosing a lifestyle that permits healthy ageing,
  diagnosing longevity, and/or
  diagnosing healthier gut microflora-host interactions,
the biomarkers can equally well be applied in a method for
  diagnosing a lifestyle that favors the development of ageing related chronic inflammatory disorders,
  diagnosing a lifestyle that is likely to prevent healthy ageing,
  diagnosing a risk for a shortened lifespan, and/or
  diagnosing unhealthier gut microflora-host interactions.

In further aspects, the present invention provides methods for:
  delaying, avoiding and/or preventing the development of ageing related chronic inflammatory disorders,
  promoting healthy ageing,
  promoting longevity,
  reducing a risk for a shortened lifespan,
  promoting healthier gut microflora-host interactions, and/or
  preventing unhealthier gut microflora-host interactions.

Typically such methods comprise a step of performing a diagnostic method as described herein on a subject; and modifying a lifestyle of the subject based on a result thereof.

For instance, the method may comprise modifying a lifestyle of the subject if a result of the diagnostic step indicates:
  an increased likelihood of the development of ageing related chronic inflammatory disorders,
  a lifestyle that is likely to prevent healthy ageing,
  a risk for a shortened lifespan, and/or
  unhealthier gut microflora-host interactions; in the subject.

The modification in lifestyle in the subject may be any change as described herein, e.g. a change in diet, a different job, more sleep, less alcohol, more challenges, less stress, less smoking, more sports, a different working and/or living environment, for example.

Preferably the change is the use of at least one nutritional product that was previously was not consumed or consumed in different amounts, e.g. a nutritional product that has an effect on healthy ageing and/or on avoiding ageing related chronic inflammatory disorders (including food products, drinks, pet food products, food supplements, nutraceuticals, food additives or nutritional formulas).

Modifying a lifestyle of the subject also includes indicating a need for the subject to change his/her lifestyle, e.g. prescribing, promoting and/or proposing a lifestyle change as described above to the subject. For instance, the method may comprise a step of administering or providing at least one nutritional product as described above to the subject.

Further advantages and features of the present invention are apparent from the following Tables, Examples and Figures.

Table 1 shows demographic, clinical characteristics of the recruited aging cohort. Values are presented as mean (±SD) with the range in parentheses. 1BMI=body mass index, 2-Diabetes mellitus: history of diabetes, fasting glucose plasma≥126 mg/dl, 3HDL=high density lipoprotein, 4LDL=low density lipoprotein, 5MMSE=Cognitive function measure using the Mini-Mental State Examination (MMSE). The score used in the analysis was corrected by age and years of educations for old people. MMSE for elderly cognitive impairment was graded as severe (score 0-17), mild (score 18-23), or not present (score 24-30). MMSE for centenarians≥20 absence of severe cognitive decline; <12 presence of severe cognitive decline. 6CRP=C reactive protein 7A-SAA=Serum amyloid A (SAA) proteins.

Table 2 display characteristic and model summary for the discriminant model between the selected aging groups.

Table 3 shows all significantly regulated metabolites in urine for the 3 age groups detected by 1H-NMR. To gain semi-quantitative information, peak areas in the original spectra were integrated for these three metabolites and differences with statistical significance were confirmed by using Wilcoxon Rank Sum test and marked as follow $*p<0.05$, $p<0.01$, $*p<0.001$.

Table 4 display all significantly regulated metabolites in blood serum for the 3 age groups detected by LC-MS. Values are expressed as mean values±SD, and marked as follows: $*p<0.05$, $p<0.01$, $*p<0.001$.

Table 5 display concentration levels (ng/100 μl) of inflammatory markers in serum for the 3 age groups analyzed by UPLC-ESI-MS/MS, and marked as follows: $*p<0.05$, $p<0.01$, $*p<0.001$ FIG. 1 represent typical urine 600 Mhz profiles from the aging cohort displaying peaks arising from major low molecular weight molecules, such as ketone bodies, organic acids, amino acids, as well as metabolites deriving from both mammalian and gut microbial metabolism (PAG AND PCS).

Figure 5A:
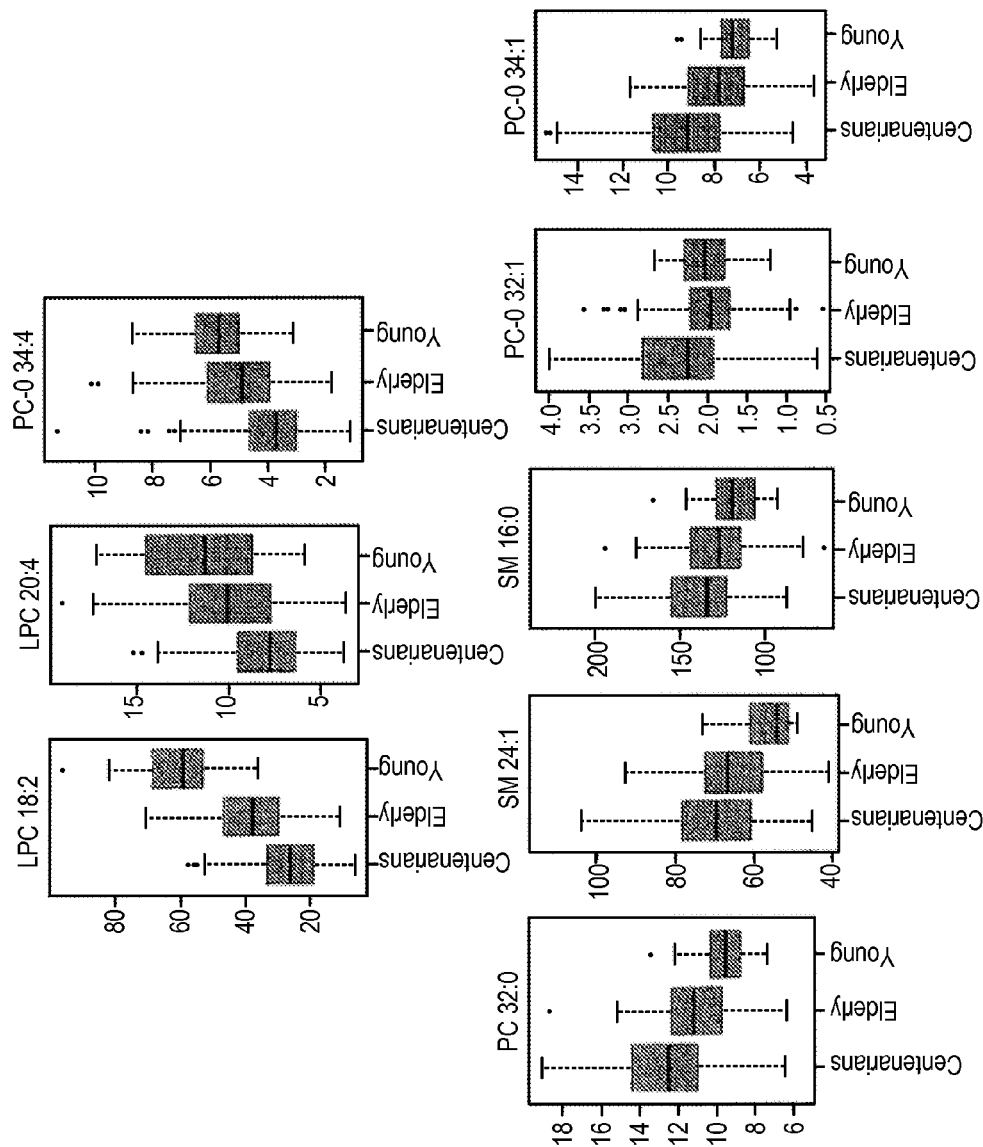
Figure 5B:
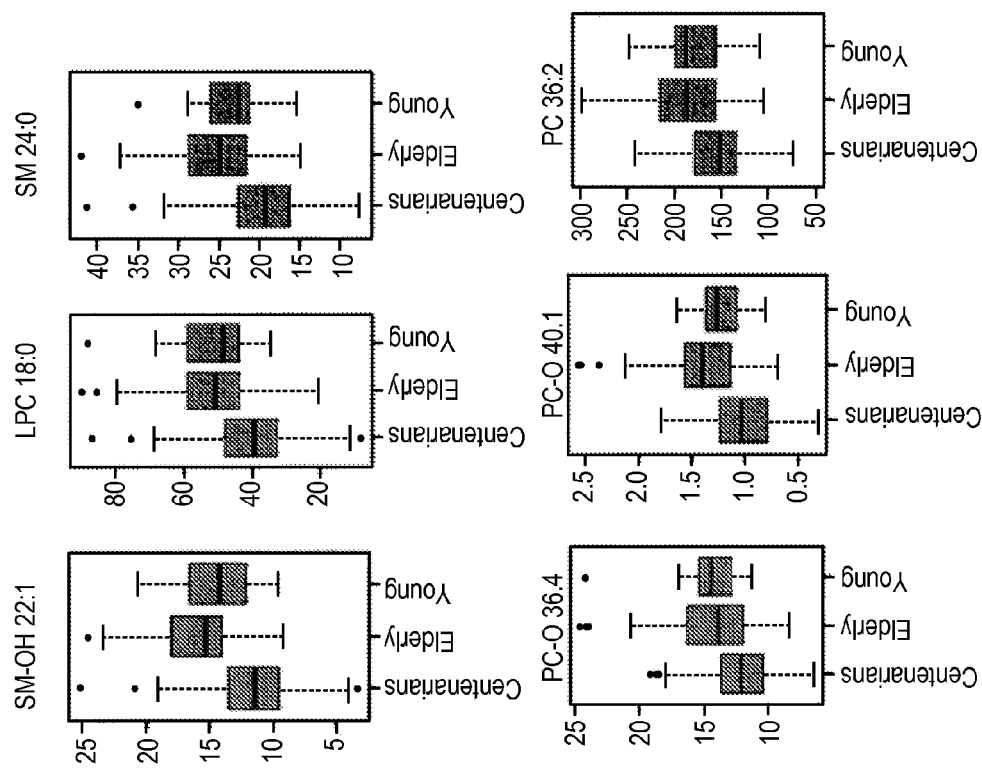

FIGS. 5A-5B show differences in lipidomic profiles (mean lipid concentrations) between the three aging time points measured by targeted UPLC-ESI-MS/MS metabonomic analysis. Box plots represent changes from left to right denoting centenarians, elderly and young individuals. Concentration is in μM. Mean values±SD from the targeted MS on the three aging groups and statistical significance were confirmed by using Wilcoxon Rank Sum test and listed in table 4. Only significant differences are displayed and were assessed by Mann-Whitney U test.

Figure 6:
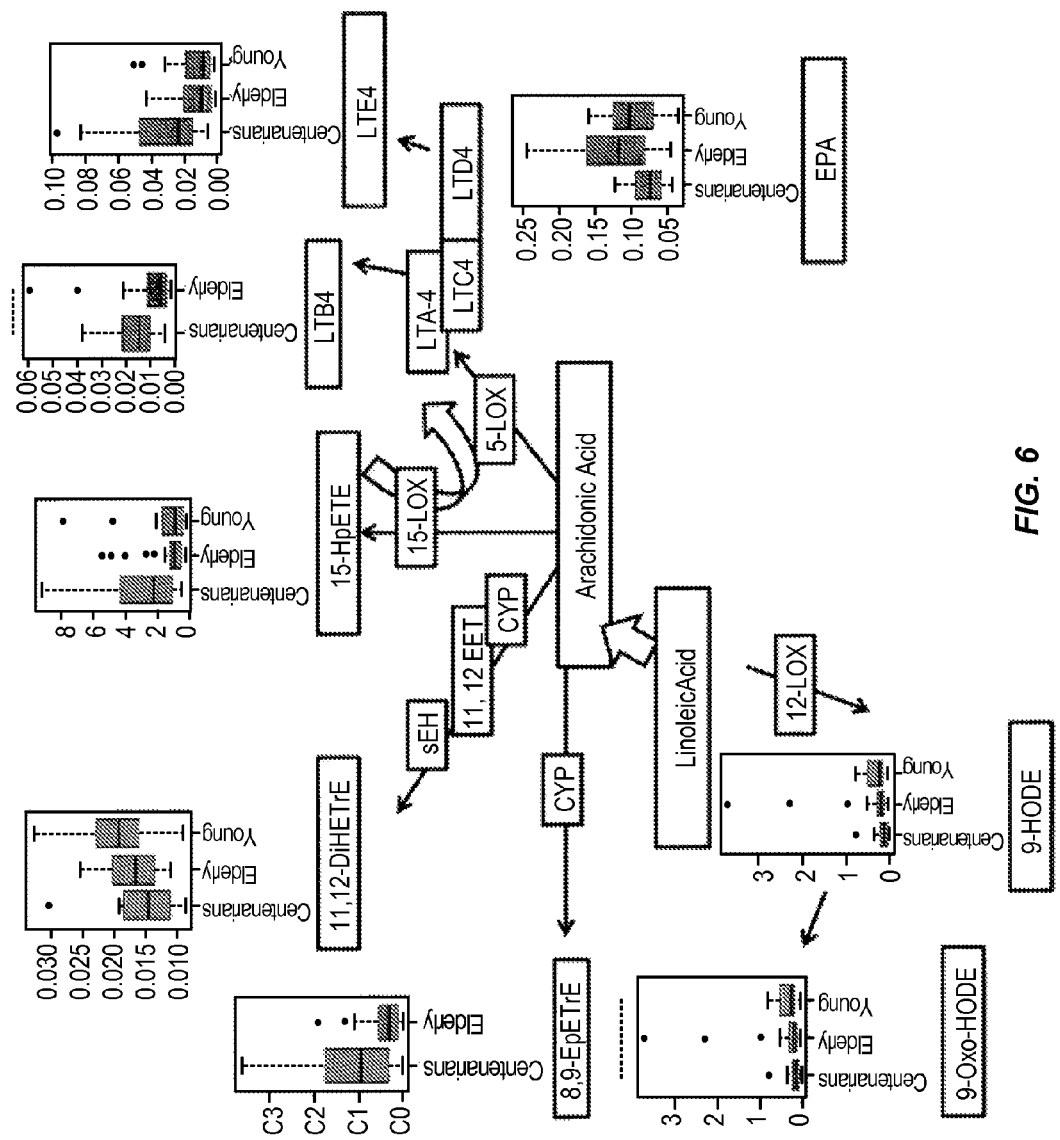

FIG. 6 shows differences in lipidomic profiles (Results are expressed in ng/100 μl and represent mean lipid concentrations) between the three aging time points measured by targeted UPLC-ESI-MS/MS metabonomic analysis. Box plots represent changes from left to right denoting centenarians, elderly and young individuals. Mean values±SD from the targeted MS on the three aging groups and Statistical significance were confirmed by using Wilcoxon Rank Sum test and listed in table 5. Only significant differences are displayed and were assessed by Mann-Whitney U test.

Examples:

Subjects and Study Groups

Each individual and their family gave informed consent for the study to take place. Overall, 541 subjects belonging to different age groups were enrolled for this study in North Italy which includes Bologna, Florence, Parma, Milan. The centenarians were composed by 156 individuals (125 females and 31 males), the elderly group was composed by 363 individuals (205 females and 158 males), the young adults group was composed by 22 individuals (10 females and 12 males).

The study protocol was approved by the Ethical Committee of Sant'Orsola-Malpighi University Hospital (Bologna, Italy). The resulting biological samples (serum and urine) were stored at −80° C. until metabolomic analysis.

Clinical Chemistry

Serum total, high density lipoprotein cholesterol (HDL) and triglyceride concentrations were measured with respective enzymatic kits from Roche Diagnostics using an autoanalyzer (Roche Diagnostics Hitachi 917, Hitachi Ltd, Tokyo, Japan). Low density lipoprotein cholesterol (LDL) concentrations were calculated using the formula of Friedewald (Friedewald W T, et al., Clinical Chemistry 18 (6): 499-502). Cytokines, including mouse interferon gamma (IFNγ), interleukin 1 beta (IL-1β), interleukin 6 (IL-6), interleukin 10 (IL-10), interleukin 12 p70 (IL-12 p70), keratinocyte derived chemokine (KC) and tumor necrosis factor (TNF), were measured using a mouse pro-inflammatory multiplex kit (Meso Scale Discoveries, Gaithersburg, Md., USA). Assay was carried out according to the manufacturer's manual. High-sensitivity C-reactive protein (CRP) was measured using a sensitive double antibody sandwich ELISA with rabbit antihuman CRP and peroxidase conjugated rabbit anti-human CRP.

Sample preparation for 1H NMR Spectroscopy. 1 ml of urine sample from the three aging groups were dried in a freeze drying apparatus (Freeze-Dryer Fisher Scientific) and adjusted to pH 6.8 using 580 μL of a phosphate buffer solution (KH2PO4, final concentration of 0.2 M) containing 1 mM of sodium 3-trimethylsilyl)-[2,2,3,3-2H4]-1-propionate (TSP), and introduced into 5 mm NMR tubes. Metabolic profiles were measured on a Bruker Avance III 600 MHz spectrometer equipped with an inverse 5 mm cryogenic probe at 300 K (Bruker Biospin, Rheinstetten, Germany). For each urine sample 1H NMR spectra were registered using pulse sequences including a standard 1H detection with water suppression. The standard spectra were acquired with a relaxation delay of 4 s and a mixing time tm of 100 ms. Acquired 1H NMR spectra were processed using the Topspin software package (version 2.1; Bruker Biospin, Rheinstetten, Germany) and were referenced to the standard (TSP) at δ=0.0. The peak assignment to specific metabolites was achieved using an internal library of compounds and the literature and confirmed by standard two-dimensional NMR spectroscopy (JRES, TOCSY, HSQC, HMBC) on selected samples. For statistical analysis all NMR spectra were converted into 12 K data points over the range of δ 0.4-10.0 and imported into the MATLAB software (version 7.11.0 (R2010b); The MathWorks Inc., Natick, Mass.) excluding the water residue (water δ=4.7120-4.84). The spectra were normalized to the total sum of all intensities within the specified range.

Sample Preparation for Biocrates Life Sciences AbsoluteIDQ™ kit Analysis. The Biocrates Life Sciences AbsoluteIDQ™ kit was used for serum samples from selected aging cohort as previously published (Römisch-Margl, W., C. Prehn, R. Bogumil, C. Röhring, K. Suhre, J. Adamski, Procedure for tissue sample preparation and metabolite extraction for high-throughput targeted metabolomics. Metabolomics, 2011. Online First). Well plate preparation and sample application and extraction were carried out according to the manufacturer's instructions. A final volume of 10 μl of serum was loaded onto the provided 96-well plate, containing isotopically labeled internal standards. Liquid chromatography was realized on a Dionex Ultimate 3000 ultra high pressure liquid chromatography (UHPLC) system (Dionex AG, Olten, Switzerland) coupled to a 3200 Q TRAP mass spectrometer (AB Sciex; Foster City, Calif., USA) fitted with a TurboV ion source operating in electrospray ionization (ESI) mode. Sample extracts (20 μl) were injected two times (in positive and negative ESI modes) via direct infusion using a gradient flow rate of 0-2.4 min: 30 μl/min, 2.4-2.8 min: 200 μl/min, 2.9-3 min: 30 μl/min. MS source parameters were set at: desolvation temperature (TEM): 200° C., high voltage: −4500 V (ESI−), 5500 V (ESI+), curtain (CUR) and nebuliser (GS1 and GS2) gases: nitrogen; 20, 40, and 50 psi; respectively, nitrogen collision gas pressure: 5 mTorr. MS/MS acquisition was realised in scheduled reaction monitoring (SRM) mode with optimised declustering potential values for the 163 metabolites screened in the assay. Raw data files (Analyst software, version 1.5.1; AB Sciex, Foster City, Calif., USA) were imported into the provided analysis software MetIQ to calculate metabolite concentrations. List of all detectable metabolites is available from Biocrates Life Sciences, Austria (http://biocrates.com). Sample preparation and inflammation markers quantification by UPLC-ESI-MS/MS using isotope dilution technique.

Based on previously published work (Naga, et. al, PROG. LIPID RESEARCH, 2001, 40, 199-299) a method to measure a panel of 63 inflammatory markers was developed in house. 300 μl of serum samples from remaining available biological material from the three age groups (n=15 centenarians, n=30 elderly, n=50 young adults) were homogenized with 10 μl of BHT-buffer (butylated hydroxytoluene; 79.2 mg/ml PBS) using the FastPrep® 24 system. For each sample a total of 50 μl of serum was mixed with 5 μl of the internal standard solution (0.1 ng/μl). The mixture was acidified by adding 15 μl of citric acid (1N). To precipitate the proteins, a volume of 550 μl of methanol/ethanol (1:1, v:v) was added and samples were mixed during 15 min at 4° C. before being centrifuged (3500 rpm, 10 min, 4° C.). The organic phase was evaporated to dryness under constant nitrogen flow and the residues were solubilised with 80 µl water, followed by the addition of 20 µL of acetonitrile, before being centrifuged at 3500 rpm for 1 min at 4° C. The supernatant was transferred into LC-MS vials before analysis. Analyses were carried out by liquid chromatography coupled to tandem mass spectrometry (LC-MS/MS). LC was realized on a Dionex Ultimate 3000 ultra pressure liquid chromatography (UPLC) system (Dionex AG, Olten, Switzerland). MS detection was realized on a 5500 Q TRAP mass spectrometer (AB Sciex; Foster City, Calif., USA) operating in ESI mode. Gradient chromatographic separation was performed on an Acquity BEH C18 column (2.1×150 mm, 1.7 µm; Waters, Milford, USA). The injection volume was 5 µl and the column was maintained at 50° C. The mobile phase consisted of water containing 1% acetic acid (eluent A) and acetonitrile (eluent B) at a constant flow rate set at 450 µl/min. Gradient elution started from 20% B with a linear increase to 50% B at 6 min, from 50% to 95% B at 13 min, hold for 3 min at 95% B, before going back to 20% B at 16.1 min and reequilibration of the column for additional 11 min. Analytes were monitored in the scheduled selected reaction monitoring (scheduled SRM) mode provided within the Analyst software (version 1.5.1; AB Sciex, Foster City, Calif., USA). All mass transitions and MS source parameters are given in supplementary data. The SRM detection window time was set at 120 sec with a target scan time of 0.5 sec. Nitrogen was used as curtain and desolvation gas at the respective pressure of CUR: 20, GS1: 70, GS2: 20 (arbitrary unit). Block source temperature was maintained at 600° C., with the respective voltages: ISV: −4000 V, EP: −10 V, CXP: −5 V. A 15-points calibration curve was realized prior to sample analysis by measuring different dilutions of the standard solution (0-10 ng). Data processing was realized using Analyst software (version 1.5.1; AB Sciex, Foster City, Calif., USA). Peak area ratio of each analyte versus its corresponding internal standard or surrogate marker was calculated. It is worth to mention that PGJ2, PGF2a, PGE2, PGE1, 15-oxo-HETE, 15-deoxy-Δ12,14-PGJ2, 6-keto PGF1a, and 5-oxo-ETE were below their detection limit in serum samples and therefore were not taken into account for statistical analysis.

Multivariate Data Analysis (MVA)

MVA was performed in several software environments. Thus, data import and pre-processing steps for both 1H NMR and targeted MS data were done using 'in-house' routines written in MATLAB (version 7.11.0, The Mathworks Inc., Natick, Mass., USA). In NMR data analysis OPLS-DA models were carried out by using the SIMCA-P+ software (version 12.0, Umetrics AB, UmeU, Sweden). Targeted MS data was analyzed by Random Forests by using the package 'randomForest'(A. Liaw and M. Wiener (2002). Classification and Regression by randomForest. R News 2(3), 18-22.) running in the R environment (R Development Core Team (2011). R: A language and environment for statistical computing. R Foundation for Statistical Computing, Vienna, Austria. ISBN 3-900051-07-0, URL http://www.R-project.org/.). Finally, univariate significance tests for confirmation were also performed in R.Clinical characteristics of the aging cohort.

Physical and biochemical characteristics of the aging cohort are shown in Table 1. BMI (p<0.001), homeostatic model assessment (HOMA) (p<0.001), total cholesterol (p=0.001), triglycerides (p=0.004), HDL (p=0.001), and LDL (p=0.04) are lower in centenarians, while serum amyloid A (A-SAA) proteins (p<0.001), and C-reactive protein (CRP) (p<0.001) are higher in centenarians, compared to elderly. Elderly display higher BMI (p<0.001), total cholesterol (p<0.001), triglycerides (p<0.001), LDL (p<0.05), and CRP (p<0.001), compared to young individuals.

Figure 1:
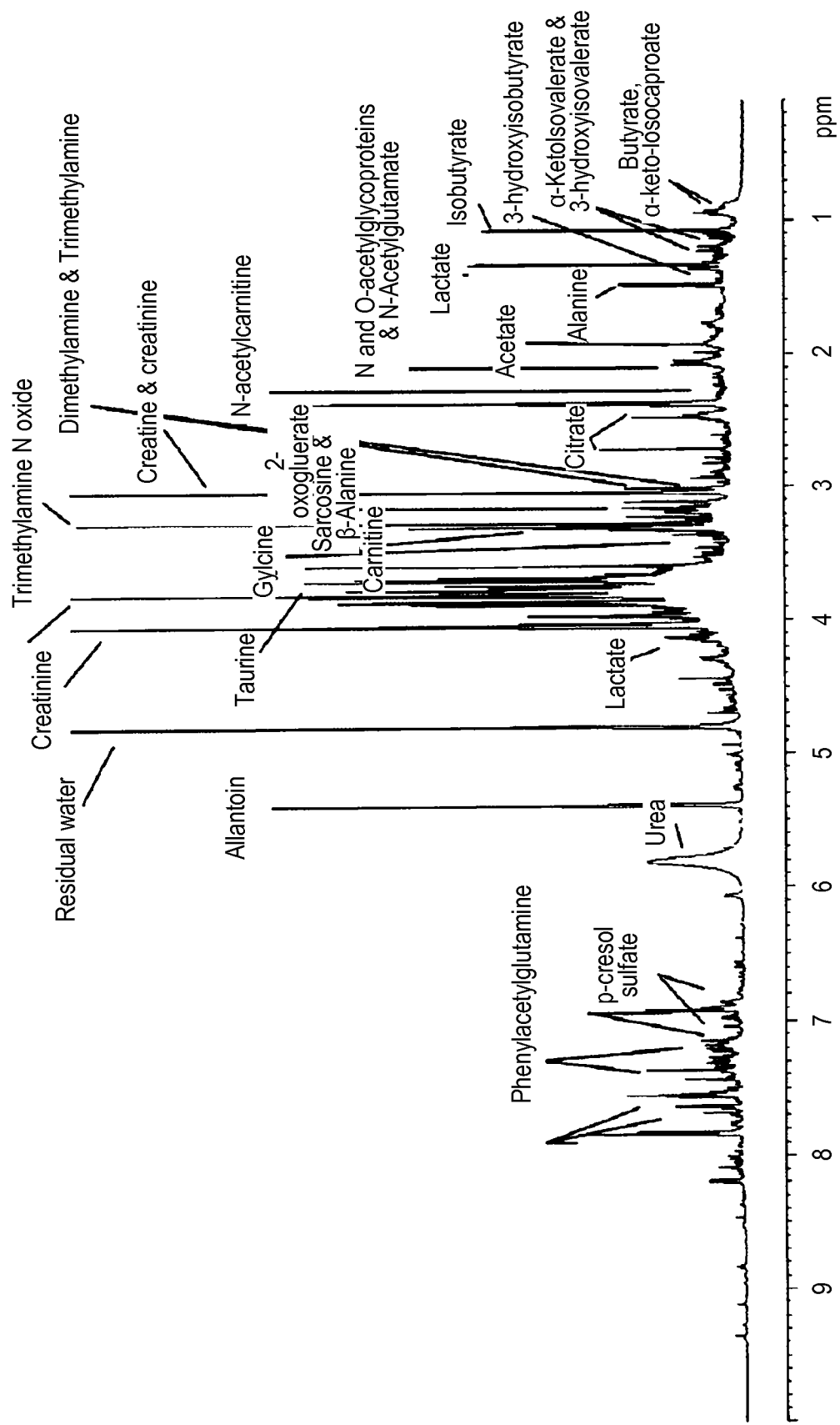
Figure 2A:
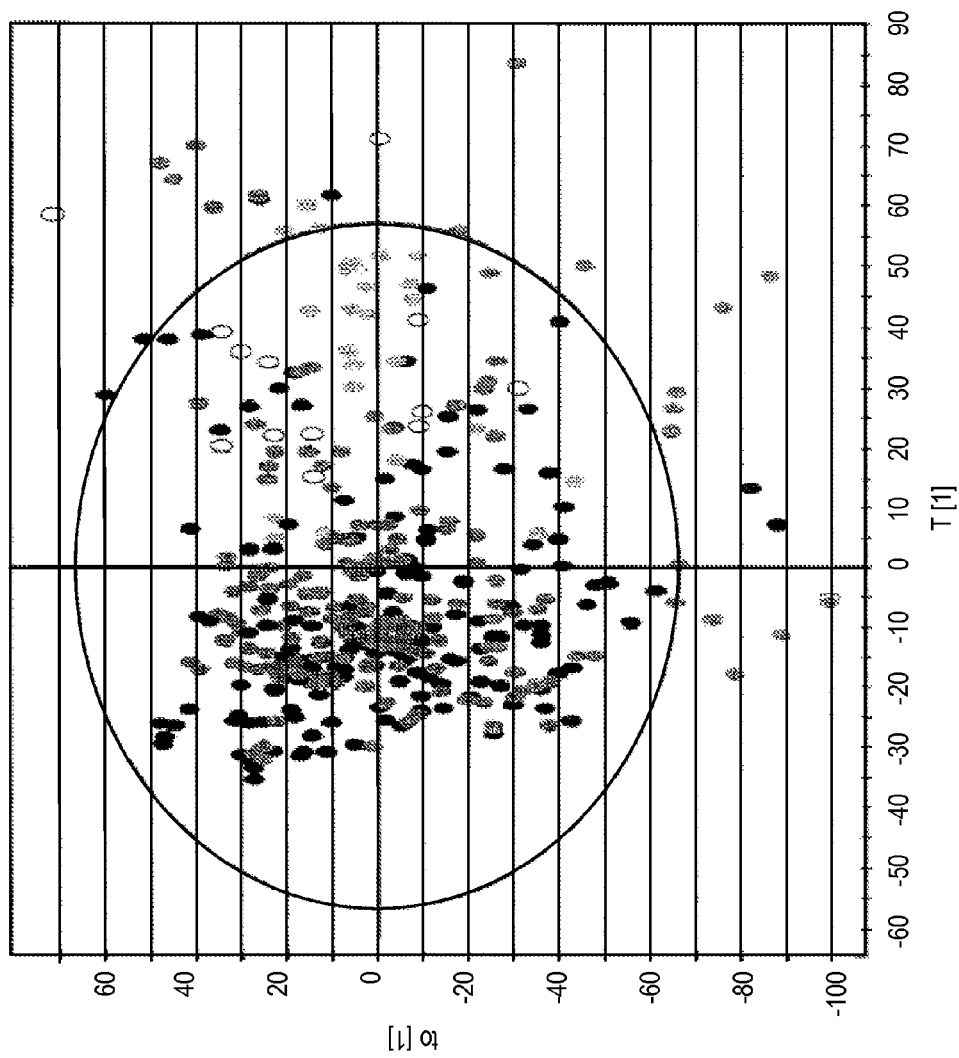
FIG. 2A shows OPLS-DA score from urinary 1H-NMR spectra from elderly and centenarians.
Figure 2B:
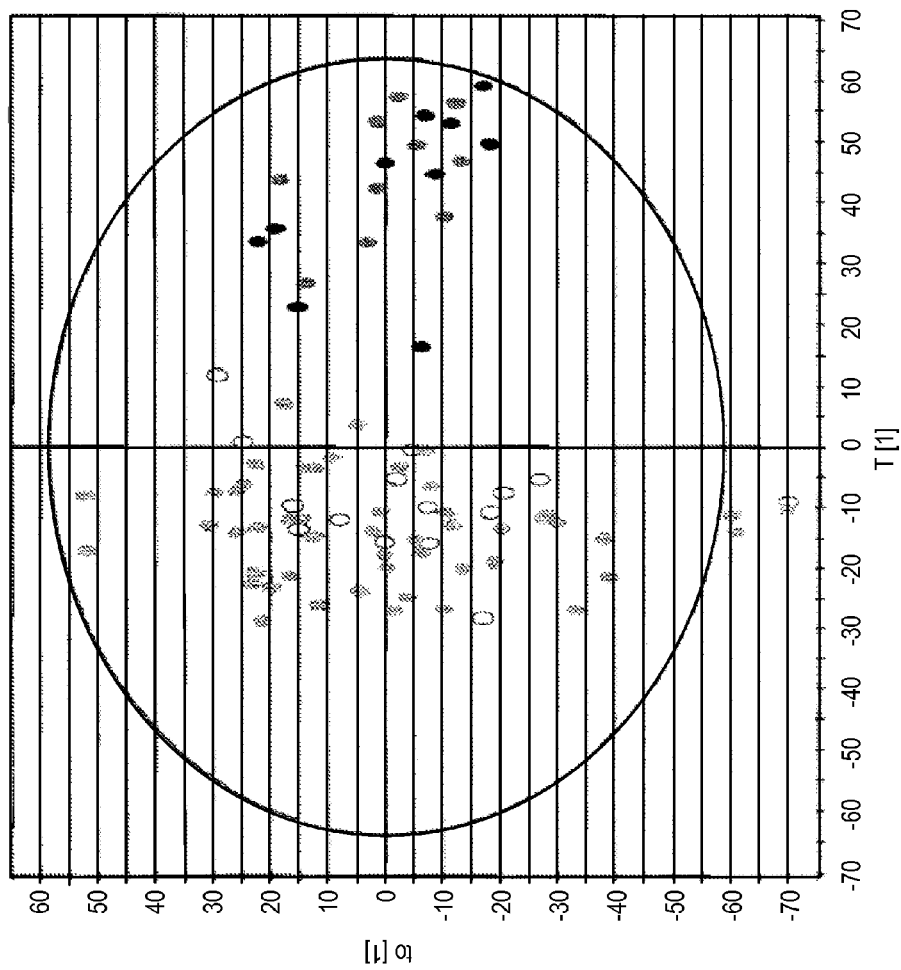
FIG. 2B shows OPLS-DA score from young adults and centenarians.
Figure 3:
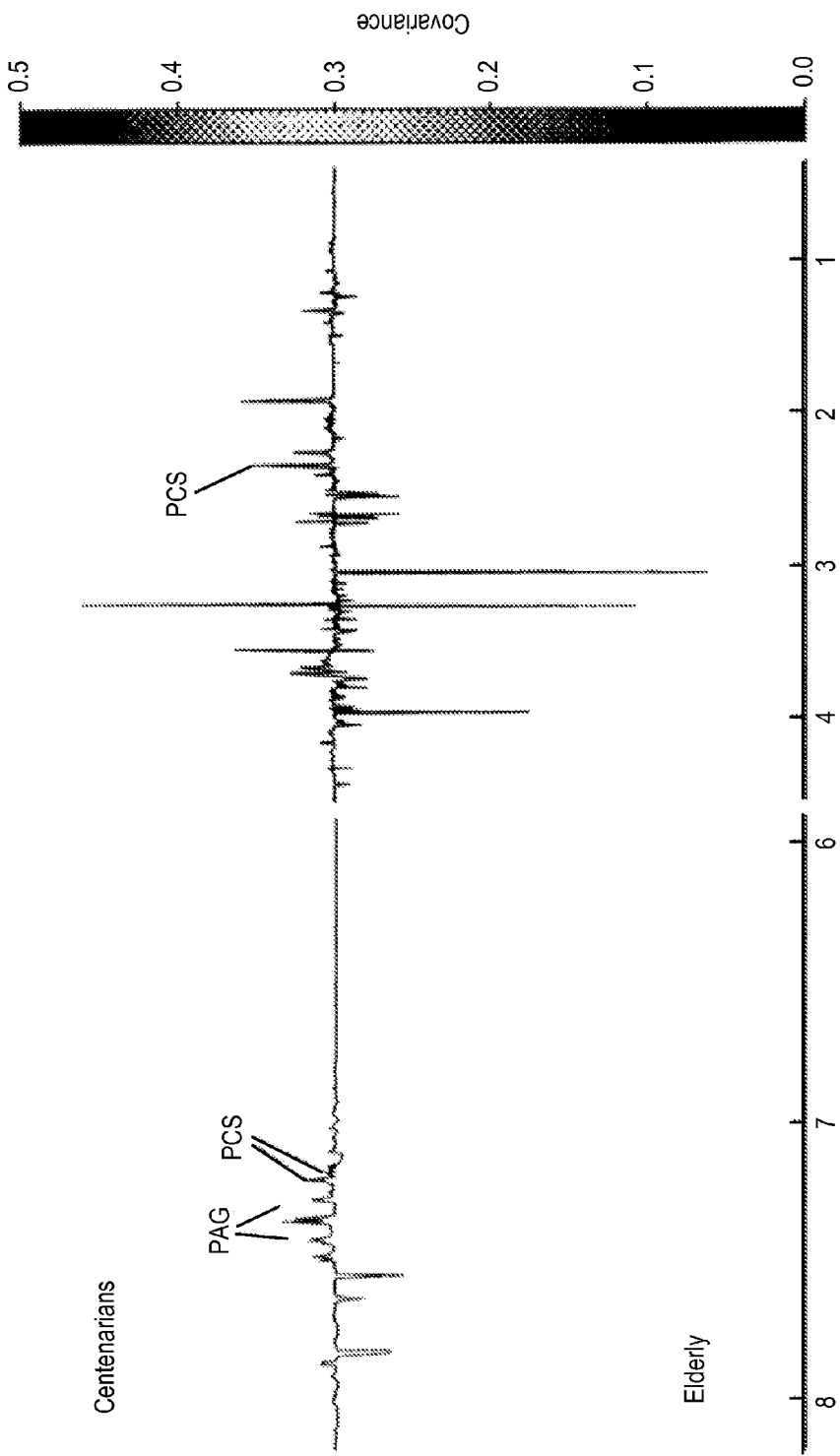
FIG. 3 shows coefficient plot derived from urinary 1H-NMR spectra from elderly and centenarians.
Figure 4:
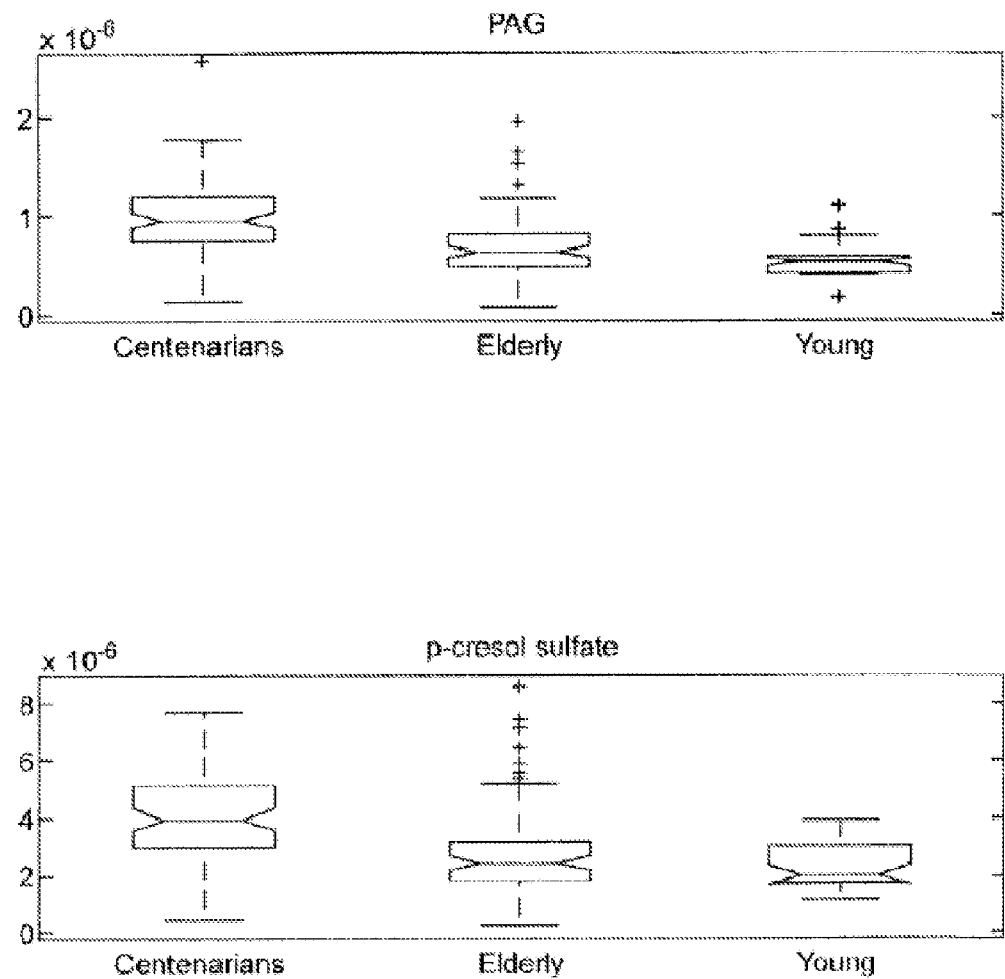
FIG. 4 shows box plots on semi-quantitative information, derived from peak areas (area under the curve) in the original spectra for PAG and PCS. Statistical significance were confirmed by using Wilcoxon Rank Sum test and listed in table 3.

Urine 600 MHz 1H-NMR from the available samples of the three aging groups (92 centenarians, 283 elderly, and 21 young adults) was used for metabolic profiling. To explore age induce changes and metabolic differences between the three age groups and minimize any effects of nonrelevant metabolite variability, supervised chemometric analysis of the urine NMR profiling was applied on the full resolution NMR data set from the three time-points. Orthohogonal Projection on Latent Structures-Discriminant Analysis (OPLS-DA) was carried out on unit variance scaled data (FIGS. 2A-B). The discriminant model between centenarians and young adults groups provided a validation error of the classifier (expressed as area under the ROC curve, AuROC (Fawcett, T., An introduction to ROC analysis, Pattern Recogn. Lett., 2006, 27:861-874) of 1.0 by using a 13.7% of the spectral variance (R2X) (Table 2). Likewise, the model between centenarians and elderly groups generated a model with an AuROC validation error of 0.93 using again a 13.7% of the total X variance (Table 2). To determine the metabolic signatures associated to the differences between age groups, loadings of the first predictive component of the OPLS-DA model were used, color coded according to the correlation coefficient of the variable [30] (FIG. 3). Accordingly, the urine discriminant model between centenarians and elderly individuals displays relatively higher amount of phenylacetylglutamine (PAG), p-cresol-sulfate (PCS). To gain semi-quantitative information, peak areas in the original spectra were integrated for these three metabolites and differences with statistical significance were confirmed by using Wilcoxon Rank Sum test (FIG. 4, Table 3). Together, the results display that the gut microbial is highly implicated in the longevity process. Targeted and quantitative LC-MS metabonomics displayed aging-associated metabolic changes in serum.

To determine age related metabolic differences in serum a targeted LC-MS/MS metabonomic approach was applied on the available biological samples from the 3 aging groups (143 centenarians, 90 elderly and 20 young adults). Multivariate data analysis was performed using Random Forests (RF™) (Breiman, L., Random Forests, Machine Learning, 2001, 45:5-32) on pre processed semi-quantitative data on 160 metabolites, including amino acids, sugars, acyl-carnitines, sphingolipids, and glycerophospholipids. Using the variable importance feature implemented in RF™, it was possible to determine the metabolic signature that discriminates better the three aging groups. To assess the individual discriminant ability of each component of the signature, Wilcoxon Rank sum tests among the age groups were performed (all significantly regulated metabolites are listed in Table 4). While the overall concentration of glycerolphospholipids and sphingolipids increase and decrease depending on the fatty acid composition, three consistent trends become apparent: set of compounds that increase or decrease (statistically valid) with age such as decrease concentration of lysophospatidylcholines (LPC 18:2, LPC 20:4), increase levels of PC 32:0, and increase concentration of sphingomyelins (SM 24:1, SM 16:0); (ii) set of compounds specific to centenarians only, with no statistical changes among elderly and young individuals, as decrease in sphingomyelins and specific glycerophospholipids (SM-OH 22:1, LPC 18:0, SM 24:0, PC-O 34:3, PC-O 36:4, PC-O 40:1, PC 36:2) and increase in specific glycerophospholipids (PC-O 32:1, PC-O 34:1).

In addition, over the remaining available serum samples from the 3 aging groups (12 centenarians, 37 elderly and 18 young adults) a targeted LC-MS/MS method was employed to investigate concentration changes in eicosanoid synthesis. Here, RF™ on quantitative data displayed statistical relevant changes among the three age groups (FIG. 6). Statistical significances among the age groups were assessed by Wilcoxon rank sum test (all significantly regulated metabolites are listed in supplementary Table 5). Centenarians display lower concentration of 11,12-dihydroxy-eicosatrienoic acid (11,12-DiHETrE), 9-hydroxyoctadecadienoic acid (9-HODE), and 9-oxo-octadecadienoic acid (9-oxo-HODE), while at the same time increase concentrations of 15-hydroxy-eicosatetraenoic acid (15-HETE), and leukotriene E4 (LTE4). Compared to elderly levels of eicosapentaenoic acid (EPA) decreased in centenarians. Furthermore, pair-wise MRC analysis between centenarians and elderly was applied to maximize changes in these two age groups displaying increase serum concentration levels of 8,9-epoxyeicosatrienoic (8,9-EET) and leukotriene B4 (LTB4) in centenarians.

The present invention also provides further embodiments as disclosed in the following numbered paragraphs:

1. A method of diagnosing a lifestyle that allows to delay and/or avoid ageing related chronic inflammatory disorders, comprising
   obtaining a serum sample from a subject
   determining the level of 9-Oxo-HODE, in the sample, and
   comparing the subject's 9-Oxo-HODE level to a predetermined reference value,
   wherein the predetermined reference value is based on an average serum 9-Oxo-HODE level in a control population, and
   wherein a decreased serum 9-Oxo-HODE level in the sample compared to the predetermined reference value indicates an increased likelihood to delay and/or avoid ageing related chronic inflammatory disorders.

2. A method of diagnosing a lifestyle that allows to delay and/or avoid ageing related chronic inflammatory disorders, comprising
   obtaining a serum sample from a subject
   determining the level of SM-OH 22:1, in the sample, and
   comparing the subject's SM-OH 22:1 level to a predetermined reference value,
   wherein the predetermined reference value is based on an average serum SM-OH 22:1 level in a control population, and
   wherein a lower serum SM-OH 22:1 level in the sample compared to the predetermined reference value indicates an increased likelihood to delay and/or avoid ageing related chronic inflammatory disorders.

3. The method of paragraph 1 or paragraph 2, further comprising
   determining the level of at least one of PC-O 40:1, SM-OH 22:1, LPC 18:0, SM 24:0, PC-O 34:1, 9-HODE, 9-oxo-HODE, or LTE4 in the sample, and
   comparing the subject's level of at least one of PC-O 40:1, SM-OH 22:1, LPC 18:0, SM 24:0, PC-O 34:1, 9-HODE, 9-oxo-HODE, or LTE4 to a predetermined reference value,
   wherein the predetermined reference value is based on average serum PC-O 40:1, SM-OH 22:1, LPC 18:0, SM 24:0, PC-O 34:1, 9-HODE, 9-oxo-HODE, or LTE4 level in a control population, and
   wherein a decreased serum PC-O 40:1, SM-OH 22:1, LPC 18:0, SM 24:0, PC-O 40:1, 9-HODE, and/or 9-oxo-HODE level in the sample compared to the predetermined reference values indicate an increased likelihood to delay and/or avoid ageing related chronic inflammatory disorders, and/or
   wherein increased serum LTE4 and/or PC-O 34:1 levels in the sample compared to the predetermined reference values indicate an increased likelihood to delay and/or avoid ageing related chronic inflammatory disorders.

4. The method of one of paragraphs 1 to 3, wherein the precision of the diagnosis is increased by also assessing whether one or more of the following biomarkers PC-O 32:1, 15-HpETE, LTB4, 8,9 EpETre is increased in serum, and/or whether one or more of the following biomarkers PC-O 34:3, PC-O 36:4, PC 36:2, 11,12-DiHETre are decreased in serum, compared to a reference value previously obtained.

5. An in vitro method of diagnosing a lifestyle that allows to delay and/or avoid ageing related chronic inflammatory disorders, comprising
   obtaining a urine sample from a subject
   determining the level of p-cresol sulphate (PCS), in the sample, and
   comparing the subject's PCS level to a predetermined reference value,
   wherein the predetermined reference value is based on an average urine PCS level in a control population, and
   wherein an elevated urine PCS level in the sample compared to the predetermined reference value indicates an increased likelihood to delay and/or avoid ageing related chronic inflammatory disorders.

6. The method of paragraph 5, further comprising
   determining the level of phenylacetylglutamine (PAG) in the sample, and
   comparing the subject's PAG level to a predetermined reference value,
   wherein the predetermined reference value is based on average urine PAG level in a control population, and
   wherein elevated urine PCS and PAG levels in the sample compared to the predetermined reference values indicate an increased likelihood to delay and/or avoid ageing related chronic inflammatory disorders.

7. A non-invasive method of diagnosing a lifestyle that allows to delay and/or avoid ageing related chronic inflammatory disorders, comprising
   obtaining a urine sample from a subject
   determining the level of phenylacetylglutamine (PAG), in the sample, and
   comparing the subject's phenylacetylglutamine (PAG), level to a predetermined reference value,
   wherein the predetermined reference value is based on an average urine PAG level in a control population, and
   wherein an elevated urine PAG level in the sample compared to the predetermined reference value indicates an increased likelihood to delay and/or avoid ageing related chronic inflammatory disorders.

8. The method of paragraph 7, further comprising
   determining the level of p-cresol sulphate (PCS) in the sample, and
   comparing the subject's PCS level to a predetermined reference value,
   wherein the predetermined reference value is based on average urine PCS level in a control population, and
   wherein elevated urine PAG and PCS levels in the sample compared to the predetermined reference values indicate an increased likelihood to delay and/or avoid ageing related chronic inflammatory disorders.

9. The method of one of paragraphs 1 to 8 to diagnose a lifestyle that permits healthy ageing.

10. The method of one of paragraphs 1 to 9 to diagnose longevity.
11. The method of one of paragraphs 1 to 10 to diagnose healthier gut microflora-host interactions.
12. The method of paragraph 11, wherein the healthier gut microflora-host interactions are diagnosed in elderly.
13. The method of one of paragraphs 1 to 12 to diagnose a healthier lifestyle, wherein the predetermined reference values are based on serum or urine levels obtained from the subject before a change in lifestyle.
14. The method in accordance with paragraph 13, wherein the change in lifestyle is a change in the diet.
15. The method in accordance with paragraph 14, wherein the change in the diet is the use of at least one nutritional product that was previously was not consumed or consumed in different amounts.
16. The method in accordance with paragraph 14 or 15 to test the effectiveness of a new nutritional regimen.
17. The method of one of paragraphs 1 to 16 wherein the levels of the biomarkers are determined by $^1$H-NMR and/or mass spectrometry in the sample and in the reference.
18. The method of one of paragraphs 1 to 17 to diagnose a healthier lifestyle, wherein the predetermined mean reference mean values are
    2 µM for 1-O-alkyl-2-acylglycerophosphocholine (PC-O) 32:1,
    7.80 µM for 1-O-alkyl-2-acylglycerophosphocholine (PC-O) 34:1,
    1.25 µg/100 µl serum for 15-hydroxy-eicosatetraenoic acid (15-HpETE),
    0.013 µg/100 µl serum for Leukotriene E4 (LTE4),
    0.020 µg/100 µl serum for Leukotriene B4 (4LTB), and/or
    0.070 µg/100 µl serum for 8,9-epoxyeicosatrienoic (8,9 EpETre)
    16.07 µM for Hydroxy-Sphingomyelin (SM-OH) 22:1,
    52.00 µM for Lysophosphatidylcholines (LPC) 18:0,
    25.00 µM for Sphingomyeline (SM) 24:0,
    5.07 µM for 1-O-alkyl-2-acylglycerophosphocholine (PC-O) 34:3,
    14.30 µM for 1-O-alkyl-2-acylglycerophosphocholine (PC-O) 36:4,
    1.41 µM for 1-O-alkyl-2-acylglycerophosphocholine (PC-O) 40:1,
    10.00 µM for Phosphatidylcholine (PC) 36:2,
    0.34 µg/100 µl serum for hydroxyoctadecadienoic acid (9-HODE),
    0.043 µg/100 µl for 9-oxo-octadecadienoic acid (9-oxo-HODE), and/or
    0.017 µg/100 µl serum for 11,12-epoxyeicosatrienoic acid (11,12-DiHETre).
19. The method according to any of paragraphs 1 to 18, further comprising:
    obtaining a urine sample from a subject
    determining the level of phenylacetylglutamine (PAG) and/or p-cresol sulphate (PCS) in the sample, and
    comparing the subject's phenylacetylglutamine (PAG) and/or PCS level to a predetermined reference value,
    wherein the predetermined reference value is based on an average urine PAG and/or PCS level in a control population, and wherein elevated urine PAG and/or PCS levels in the sample compared to the predetermined reference values indicate an increased likelihood to delay and/or avoid ageing related chronic inflammatory disorders.
20. A biomarker for the diagnosis of a lifestyle that allows delaying and/or avoiding ageing chronic inflammatory disorders, wherein the biomarker is 9-Oxo-HODE.
21. A biomarker for the diagnosis of a lifestyle that allows delaying and/or avoiding ageing chronic inflammatory disorders, wherein the biomarker is SM-OH 22:1.
22. The biomarker in accordance with paragraph 20 or 21, wherein the biomarker is to be detected in serum.
23. A biomarker for the diagnosis of a lifestyle that allows delaying and/or avoiding ageing chronic inflammatory disorders, wherein the biomarker is phenylacetylglutamine (PAG).
24. A biomarker for the diagnosis of a lifestyle that allows delaying and/or avoiding ageing chronic inflammatory disorders, wherein the biomarker is p-cresol sulphate (PCS).
25. The biomarker in accordance with paragraph 23 or 24, wherein the biomarker is to be detected in urine.
26. A method for diagnosing (i) a lifestyle that favors the development of ageing related chronic inflammatory disorders, (ii) a lifestyle that is likely to prevent healthy ageing, (iii) a risk for a shortened lifespan, and/or (iv) unhealthier gut microflora-host interactions, comprising
    obtaining a serum sample from a subject
    determining the level of 9-Oxo-HODE and/or SM-OH 22:1 in the sample, and
    comparing the subject's 9-Oxo-HODE and/or SM-OH 22:1 level to a predetermined reference value,
    wherein the predetermined reference value is based on an average serum 9-Oxo-HODE and/or SM-OH 22:1 level in a control population, and
    wherein an increased serum 9-Oxo-HODE and/or SM-OH 22:1 level in the sample compared to the predetermined reference value indicates (i) a lifestyle that favors the development of ageing related chronic inflammatory disorders, (ii) a lifestyle that is likely to prevent healthy ageing, (iii) an increased risk for a shortened lifespan, and/or (iv) unhealthier gut microflora-host interactions.
27. A method for diagnosing (i) a lifestyle that favors the development of ageing related chronic inflammatory disorders, (ii) a lifestyle that is likely to prevent healthy ageing, (iii) a risk for a shortened lifespan, and/or (iv) unhealthier gut microflora-host interactions, comprising
    obtaining a urine sample from a subject
    determining the level of PAG and/or PCS in the sample, and
    comparing the subject's PAG and/or PCS level to a predetermined reference value,
    wherein the predetermined reference value is based on an average urine PAG and/or PCS level in a control population, and
    wherein a lower urine PAG and/or PCS level in the sample compared to the predetermined reference value indicates (i) a lifestyle that favors the development of ageing related chronic inflammatory disorders, (ii) a lifestyle that is likely to prevent healthy ageing, (iii) an increased risk for a shortened lifespan, and/or (iv) unhealthier gut microflora-host interactions.
28. A method for (i) delaying, avoiding and/or preventing the development of ageing related chronic inflammatory disorders, (ii) promoting healthy ageing, (iii) promoting longevity, (iv) reducing a risk for a shortened lifespan, (v) promoting healthier gut microflora-host interactions, and/or (vi) preventing unhealthier gut microflora-host interactions, comprising:

(a) performing a diagnostic method as described in paragraph 26 or 27; and
(b) modifying a lifestyle of the subject if the subject has (i) an increased likelihood of the development of ageing related chronic inflammatory disorders, (ii) a lifestyle that is likely to prevent healthy ageing, (iii) an increased risk for a shortened lifespan, and/or (iv) unhealthier gut microflora-host interactions.

29. A method according to paragraph 28, wherein the modification in lifestyle in the subject comprises a change in diet.

30. A method according to paragraph 29, wherein the change in diet comprises administering at least one nutritional product to the subject that has an effect on healthy ageing and/or on avoiding ageing related chronic inflammatory disorders.

TABLE 1

| Factor | Centenerians | Elderly | Young |
|---|---|---|---|
| Demographic | | | |
| Gender, male/female | 31/125 | 158/205 | 12/10 |
| Age, years | $100.9^{\pm}2$ (99-111) | $70.4^{\pm}6$ (55-88) | $30.6^{\pm}5$ (25-40) |
| Clinical | | | |
| BMI[1], kg/m$^2$ | $23.8^{+}3.7$ (13.3-34.1) | $26.9^{\pm}4.6$ (16.7-54.7) | $21.92^{\pm}2.1$ (18.3.23.6) |
| HOMA | $1.90^{\pm}2.8$ (0.20-23) | $3.3^{\pm}3.1$ (0.20-28.9) | n/a |
| Diabetes[2], n | 8 | 36 | n/a |
| Cholesterol, mg/dl | $188.2^{\pm}38.1$ (110-318) | $201.0^{\pm}38.8$ (5-335) | $162.3^{\pm}28.4$ (123-207) |
| Triglycerides, mg/dl | $119.6^{\pm}65.4$ (50-535) | $125.5^{\pm}63.1$ (41-550) | $71.1^{\pm}32.1$ (28-143) |
| HDL[3], mg/dl | $47.4^{\pm}13.1$ (20-99) | $55.8^{\pm}21.1$ (20-212) | $51.3^{\pm}8.7$ (38-66) |
| LDL[4], mg/dl | $116.2^{\pm}36.1$ (27-248) | $120^{\pm}41.7$ (12-248) | $96.8^{\pm}30.1$ (49-144) |
| MMSE[5] | $20.3^{\pm}6.4$ (1.3-30.8) | $27.3^{\pm}1.9$ (1.3-31.0) | n/a |
| CRP[6], mg/L | $5.8^{\pm}6.1$ (0.28-28.2) | $2.8^{\pm}3.7$ (0.11-25.7) | $0.7^{\pm}0.4$ (0.28-2.03) |
| Heart failure, n | 44 | 4 | 0 |
| Irregular heart rhythm, n | 33 | 46 | 0 |
| Angina pectoris, n | 25 | 12 | 0 |
| A-SAA[7], μg/ml | $540^{\pm}706$ (0.01-3859.4) | $158.2^{\pm}21.9.6$ (0.01-1861.9) | n/a |
| Metabolomics | | | |
| Urine-$^1$H-NMR | 18/74 | 128/155 | 11/10 |
| Gender, male/female | | | |
| Age, years | $100.9^{\pm}2$ (99-111) | $70.1^{\pm}6$ (55-88) | $30.9^{\pm}5$ (24-40) |
| Serum-Targeted MS | 30/113 | 34/56 | 11/9 |
| Gender, male/female | | | |
| Age, years | $100.9^{\pm}2$ (99-111) | $69.6^{\pm}6$ (56-86) | $30.6^{\pm}5$ (24-40) |
| Lipidomics | | | |
| Serum-Targeted MS | 2/10 | 21/16 | 9/9 |
| Gender, male/female | | | |
| Age, years | $101^{\pm}2$ (99-104) | $70^{\pm}6$ (59-78) | $31.2^{\pm}5$ (25-40) |

TABLE 2

| Overview | $R2X_{(cum)}$ | $R2Y_{(cum)}$ | $Q^2Y$ | | AuROC |
|---|---|---|---|---|---|
| Centenarians vs. Elderly | 0.14 | 0.52 | 0.39 | 0.96 | 0.93 |
| Centenarians vs. Young | 0.14 | 0.86 | 0.75 | 1.00 | 1.00 |
| Young vs. Elderly | 0.05 | 0.21 | 0.09 | 0.92 | 0.81 |

TABLE 3

| Age group Peak Integral (a.u.) | Chemical shift | Centenarians Mean ± SD | Elderly Mean ± SD | Young Mean ± SD |
|---|---|---|---|---|
| PAG | 2.34(s) | 9.93 ± 3.72*** | 6.62 ± 2.59 | 5.89 ± 2.35 |
| PCS | 7.36 (m) | 4.06 ± 1.53*** | 2.62 ± 1.22 | 2.32 ± 0.85 |

TABLE 4

| Metabolites [μM/l] | Young Mean ± SD | Elderly Mean ± SD | Centenarians Mean ± SD |
|---|---|---|---|
| PC-O 32:1 | 2.02 ± 0.36 | 2 ± 0.51 | 2.35 ± 0.63* |
| PC-O 34:1 | 7.34 ± 1.07 | 7.88 ± 1.71 | 9.54 ± 2.19*** |
| PC-O 34:3 | 5.73 ± 1.4 | 5.07 ± 1.71 | 3.94 ± 1.54*** |
| PC-O 36:2 | 9.54 ± 1.75 | 9.58 ± 2.39 | 9.29 ± 2.26* |
| PC-O 36:4 | 14.48 ± 2.83 | 14.35 ± 3.55 | 12.39 ± 2.56* |
| PC-O 40:1 | 1.23 ± 0.23 | 1.41 ± 0.41 | 1.02 ± 0.32*** |
| LPC 18:0 | 52.18 ± 12.93 | 52 ± 13.5 | 40.4 ± 12.02** |
| SM 24:0 | 23.45 ± 4.37 | 25.64 ± 5.31 | 19.79 ± 4.92*** |
| SM-OH 22:1 | 14.52 ± 2.94 | 16.07 ± 3.37 | 11.51 ± 3.04*** |

TABLE 5

| Metabolites [μg/100 μl serum] | Young | Elderly | Centenarians |
|---|---|---|---|
| LTE4 | 0.015 ± 0.014 | 0.013 ± 0.011 | 0.035 ± 0.03*** |
| LTB4 | 0.011 ± 0.014 | 0.019 ± 0.047 | 0.016 ± 0.009* |
| EPA | 0.097 ± 0.036 | 0.123 ± 0.052 | 0.078 ± 0.026** |
| 15-HpETE | 1.512 ± 1.949 | 1.255 ± 1.245 | 3.348 ± 2.865*** |
| 11,12-DiHETrE | 0.02 ± 0.006 | 0.017 ± 0.004 | 0.016 ± 0.006* |
| 9-oxo-ODE | 0.042 ± 0.028 | 0.043 ± 0.039 | 0.022 ± 0.013*** |
| 9-HODE | 0.348 ± 0.223 | 0.397 ± 0.677 | 0.204 ± 0.211** |
| 8,9-EpETrE | 0.067 ± 0.101 | 0.074 ± 0.186 | 0.113 ± 0.107*** |

What is claimed is:

1. A method of diagnosing a lifestyle that allows a subject to delay and/or avoid an ageing related chronic inflammatory disorder, the method comprising:
    determining a level of 1-O-alkyl-2-acylglycerophosphocholine (PC-O) 40:1, in a serum sample obtained from the subject after a change in lifestyle has been made, and comparing the subject's PC-O 40:1 level to a predetermined reference value,
wherein the predetermined reference value is based on a serum PC-O 40:1 level obtained from the subject before the change in lifestyle, and
wherein a decreased serum PC-O 40:1 level in the serum sample compared to the predetermined reference value indicates an increased likelihood that the change in lifestyle allows the subject to delay and/or avoid the ageing related chronic inflammatory disorder.

2. The method of claim 1, further comprising
determining a level of at least one of hydroxy-sphingomyelin (SM-OH) 22:1, lysophosphatidylcholines (LPC) 18:0, sphingomyelin (SM) 24:0, 1-O-alkyl-2-acylglycerophosphocholine (PC-O) 34:1, hydroxyoctadecadienoic acid (9-HODE), 9-oxo-octadecadienoic (9-oxo-HODE), or leukotriene E4 (LTE4) in the serum sample, and
comparing the subject's level of at least one of SM-OH 22:1, LPC 18:0, SM 24:0, PC-O 34:1, 9-HODE, 9-oxo-HODE, or LTE4 to a predetermined reference value,
wherein the predetermined reference value is based on a serum SM-OH 22:1, LPC 18:0, SM 24:0, PC-O 34:1, 9-HODE, 9-oxo-HODE, or LTE4 level obtained from the subject before the change in lifestyle, and
wherein a decreased serum PC-O 40:1 level in the sample and/or a lower serum SM-OH 22:1, LPC 18:0, SM 24:0, PC-O 40:0, 9-HODE, or 9-oxo-HODE level in the sample compared to the predetermined reference values indicate an increased likelihood that the change in lifestyle allows the subject to delay and/or avoid the ageing related chronic inflammatory disorder, and/or
wherein increased serum LTE4, PC-O 34:1 levels in the sample compared to the predetermined reference values indicate an increased likelihood that the change in lifestyle allows the subject to delay and/or avoid the ageing related chronic inflammatory disorder.

3. The method of claim 2, further comprising assessing whether one or more of the following biomarkers PC-O 32:1, 15-hydroxy-eicosatetraenoic acid (15-HpETE), leukotriene B4 (LTB4), 8,9-epoxyeicosatrienoic (8,9EpETre) is increased in the serum sample, and/or whether one or more of the following biomarkers PC-O 34:3, PC-O 36:4, PC 36:2, 11,12-epoxyeicosatrienoic acid (11,12-DiHETre) is decreased in the serum sample, compared to a predetermined reference value based on a serum level of the one or more biomarkers obtained from the subject before the change in lifestyle.

4. The method of claim 3 to diagnose a healthier lifestyle, wherein the predetermined reference values are
2 µM for 1-O-alkyl-2-acylglycerophosphocholine (PC-O) 32:1,
7.80 µM for 1-O-alkyl-2-acylglycerophosphocholine (PC-O) 34:1,
1.25 µg/100 µl serum for 15-hydroxy-eicosatetraenoic acid (15-HpETE),
0.013 µg/100 µl serum for leukotriene E4 (LTE4),
0.020 µg/100 µl serum for leukotriene B4 (4LTB), and/or
0.070 µg/100 µl serum for 8,9-epoxyeicosatrienoic (8,9 EpETre)
16.07 µM for hydroxy-Sphingomyelin (SM-OH) 22:1,
52.00 µM for lysophosphatidylcholines (LPC) 18:0,
25.00 µM for Sphingomyeline (SM) 24:0,
5.07 µM for 1-O-alkyl-2-acylglycerophosphocholine (PC-O) 34:3,
14.30 µM for 1-O-alkyl-2-acylglycerophosphocholine (PC-O) 36:4,
10.00 µM for phosphatidylcholine (PC) 36:2,
0.34 µg/100 µl serum for hydroxyoctadecadienoic acid (9-HODE),
0.043 µg/100 µl for 9-oxo-octadecadienoic acid (9-oxo-HODE), and/or
0.017 µg/100 µl serum for 11,12-epoxyeicosatrienoic acid (11,12-DiHETre).

5. The method of claim 1, wherein the method serves to diagnose a lifestyle that permits healthy ageing.

6. The method of claim 1, wherein the method serves to diagnose longevity.

7. The method of claim 1, wherein the method serves to diagnose healthier gut microflora-host interactions.

8. The method of claim 7, wherein the subject is an elderly subject.

9. The method of claim 1, wherein the change in lifestyle is a change in diet.

10. The method of claim 9, wherein the change in diet is use of at least one nutritional product that previously was not consumed or consumed in different amounts.

11. The method of claim 9, wherein the method serves to detect the effectiveness of a new nutritional regimen.

12. The method of claim 1 wherein the level of PC-O 40:1 is determined by 1H-NMR and/or mass spectrometry in the sample.

13. The method of claim 1 wherein the method serves to diagnose a healthier lifestyle, wherein the predetermined reference value is 1.41 µM for 1-O-alkyl-2-acylglycerophosphocholine (PC-O) 40:1.

14. The method of claim 1, further comprising:
determining a level of phenylacetylglutamine (PAG) and/or p-cresol sulphate (PCS) in a urine sample from the subject after the change in lifestyle has been made, and
comparing the subject's phenylacetylglutamine (PAG) and/or PCS level to a predetermined reference value,
wherein the predetermined reference value is based on a urine PAG and/or PCS level obtained from the subject before the change in lifestyle, and wherein elevated urine PAG and/or PCS levels in the sample compared to the predetermined reference values indicate an increased likelihood that the change in lifestyle allowed the subject to delay and/or avoid the ageing related chronic inflammatory disorder.

15. A method for diagnosing (i) a lifestyle that favors the development of an ageing related chronic inflammatory disorder, (ii) a lifestyle that is unlikely to promote healthy ageing, (iii) a risk for a shortened lifespan, and/or (iv) unhealthier gut microflora-host interactions, the method comprising:
determining a level of PC-O 40:1 in a serum sample from a subject after a change in lifestyle has been made, and
comparing the subject's PC-O 40:1 level to a predetermined reference value,
wherein the predetermined reference value is based a serum PC-O 40:1 level obtained from the subject before a change in lifestyle, and
wherein an increased serum PC-O 40:1 level in the sample compared to the predetermined reference value indicates (i) a lifestyle that favors the development of the ageing related chronic inflammatory disorder, (ii) a lifestyle that is unlikely to promote healthy ageing, (iii) an increased risk for a shortened lifespan, and/or (iv) unhealthier gut microflora-host interactions.

16. A method for (i) delaying, and/or avoiding the development of an ageing related chronic inflammatory disorder, (ii) promoting healthy ageing, (iii) promoting longevity, (iv) reducing a risk for a shortened lifespan, (v) promoting healthier gut microflora-host interactions, and/or (vi) preventing unhealthier gut microflora-host interactions, comprising:
- (a) performing a diagnostic method as described in claim 15; and
- (b) modifying a lifestyle of the subject if the subject has (i) an increased likelihood of the development of an ageing related chronic inflammatory disorder, (ii) a lifestyle that is unlikely to promote healthy ageing, (iii) an increased risk for a shortened lifespan, and/or (iv) unhealthier gut microflora-host interactions.

17. The method of claim 16, wherein the modification in lifestyle in the subject comprises a change in diet.

18. The method of claim 17, wherein the change in diet comprises administering at least one nutritional product to the subject that promotes healthy ageing and/or avoids an ageing related chronic inflammatory disorder.

* * * * *